United States Patent
Watanabe et al.

(10) Patent No.: US 8,243,266 B2
(45) Date of Patent: Aug. 14, 2012

(54) SAMPLE OBSERVATION SYSTEM AND SAMPLE OBSERVATION PROCESS

(75) Inventors: Kohei Watanabe, Yokohama (JP); Tsuyoshi Nomoto, Tokyo (JP); Takeshi Miyazaki, Yokohama (JP); Toshio Tanaka, Tsu (JP); Yasuhito Shimada, Nagoya (JP)

(73) Assignee: Canon Kabushiki Kaisha, Tokyo (JP)

( * ) Notice: Subject to any disclaimer, the term of this patent is extended or adjusted under 35 U.S.C. 154(b) by 318 days.

(21) Appl. No.: 12/788,136

(22) Filed: May 26, 2010

(65) Prior Publication Data
US 2010/0302534 A1    Dec. 2, 2010

(30) Foreign Application Priority Data

May 29, 2009    (JP) ................................. 2009-131628

(51) Int. Cl.
*G01N 1/10*    (2006.01)

(52) U.S. Cl. ....................................................... 356/246

(58) Field of Classification Search ........................ None
See application file for complete search history.

(56) References Cited

U.S. PATENT DOCUMENTS

| | | |
|---|---|---|
| 2010/0300547 A1 | 12/2010 | Nomoto |
| 2010/0304428 A1 | 12/2010 | Nomoto |

FOREIGN PATENT DOCUMENTS

| | | |
|---|---|---|
| JP | 2001-059599 A | 3/2001 |
| JP | 2003-346693 A | 12/2003 |

*Primary Examiner* — Gregory J Toatley
*Assistant Examiner* — Amanda Merlino
(74) *Attorney, Agent, or Firm* — Canon U.S.A., Inc., IP Division (57) ABSTRACT

A sample observation system and a sample observation process are provided which do not need any special manipulation or treatment to limit the motion of the sample or adjust the orientation of the sample when observing the sample, and enable observation of samples simply from wider direction than ever. A sample observation system of a sample whose vertical direction is defined by gravity, wherein the system at least includes a sample holder having at least one penetrating hole for retaining a liquid containing the sample; an observation unit for observing the sample; and an angle adjusting unit for varying the angle of the observation unit to the direction of the gravity which acts on the sample in a condition in which the sample holder and the observation unit have a fixed relative angle therebetween.

7 Claims, 4 Drawing Sheets

SAMPLE OBSERVATION SYSTEM AND SAMPLE OBSERVATION PROCESS

BACKGROUND OF THE INVENTION

1. Field of the Invention

The present invention relates to an observation system for enabling simple observation of a sample from a plurality of directions, and an observation process of a sample.

2. Description of the Related Art

In recent years, effects of a gene in a biological sample on a living body have been investigated by knocking down a specific gene or introducing a foreign gene using genetic manipulation. Also effects of a chemical substance used in everyday life or a pharmaceutical product on a living body have been observed by exposing a biological sample including an embryo and an adult (individual) to a chemical substance or the like or introducing a chemical substance or the like to such a biological sample. On this account, manipulation and observation of a biological sample including an embryo and an individual have been frequently performed.

However, such biological samples are often very small and fragile, and they need careful and exact handling. Accordingly, when a biological sample is observed while limiting the motion and adjusting the direction thereof, it is generally required to manipulate the sample directly with tweezers, a needle or a micromanipulator while microscopically observing the sample. This manipulation takes skilled techniques and lacks rapidity.

In the meantime, as attempts for quickly adjusting the observation direction of the biological sample, Japanese Patent Application Laid-Open No. 2001-059599 discloses an apparatus in which the support of the stand for magnification observation can be tilted to change the observation angle, and Japanese Patent Application Laid-Open No. 2003-346693 discloses a biological sample observation process in which the biological sample can be observed from a different angle by tilting the stage for the biological sample.

Although the observation direction of the biological sample could be changed in the observation unit of the biological sample in the above publications, it was necessary to apply an anesthetic or perform observation in a highly viscous medium for limiting the motion of an actively moving biological sample. Besides, the observation direction was limited due to the mutual interference between the stage for the biological sample and the observation unit in the publications, while the observation of the biological sample from arbitrary directions allows directly manipulating.

SUMMARY OF THE INVENTION

One aspect of the present invention is to provide a sample observation system and a sample observation process which do not need any special handling or treatment to limit the motion of the sample or adjust the orientation of the sample when observing the sample (particularly biological sample) but enable observation or manipulation of an actively moving biological sample from any directions.

That is, the present invention is directed to a sample observation system of a sample whose vertical direction is defined by gravity, wherein the system at least includes a sample holder having at least one penetrating hole for retaining a liquid containing the sample; an observation unit for observing the sample; and an angle adjusting unit for varying the angle of the observation unit to the direction of the gravity which acts on the sample in a condition in which the sample holder and the observation unit have a fixed relative angle therebetween.

The present invention is also directed to a sample observation process of a sample whose vertical direction is defined by gravity, wherein the process includes retaining a liquid containing the sample in a sample holder having at least one penetrating hole; and observing the sample in a condition in which an observation unit for observing the sample and the direction of the gravity which acts on the sample have an arbitrary angle therebetween and further in a condition in which the sample holder and the observation unit have a fixed relative angle therebetween.

According to the above-mentioned sample observation system and sample observation process, the biological sample is retained in the penetrating hole and the motion thereof is thereby limited, and besides since the biological sample retains the vertical direction according to the gravitational direction independently from the observation direction by the observation unit, and the observation direction in relation to the biological sample can be varied by varying the angle of the observation unit to the direction of the gravity which acts on the sample through the manipulation of the angle adjusting unit. Therefore, observation or manipulation (intervention) of a biological sample from arbitrary angles can be enabled by adjusting observation direction freely without giving any stress and without any special means for adjusting the direction of the actively moving biological sample.

Another aspect of the present invention is a process for observing a plurality of samples simultaneously which includes disposing a plurality of biological samples respectively in positions on a plane which positions correspond to focal fields of an image acquisition unit; and rotating both the image acquisition unit and the plane around an axis on the plane while keeping the positional relationship of the image acquisition unit and the plane.

The apparatus for observing a plurality of samples simultaneously according to the present invention has an image acquisition unit; a holder for disposing a plurality of biological samples respectively in positions on a plane which positions correspond to focal fields of the image acquisition unit; and a rotation mechanism for rotating both the image acquisition unit and the plane around an axis on the plane while keeping the positional relationship of the image acquisition unit and the plane.

According to the above-mentioned aspect, states of a plurality of biological samples can be observed simultaneously from various directions.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Hereinbelow, embodiments of the present invention are described referring to the attached drawings. The individually disclosed embodiments are examples of the sample observation system and the sample observation process of the present invention and the present invention is not limited to this.

The first embodiment of the present invention is for a sample whose vertical direction is defined by the gravity and characterized by at least including a sample holder having a hole for retaining a liquid containing such a sample and an observation unit for observing the sample and an angle adjusting unit. The angle adjusting unit is to vary the angle of the observation unit to the direction of the gravity which acts on the sample in a condition in which the sample holder and the observation unit have a fixed relative angle therebetween.

Figure 4:
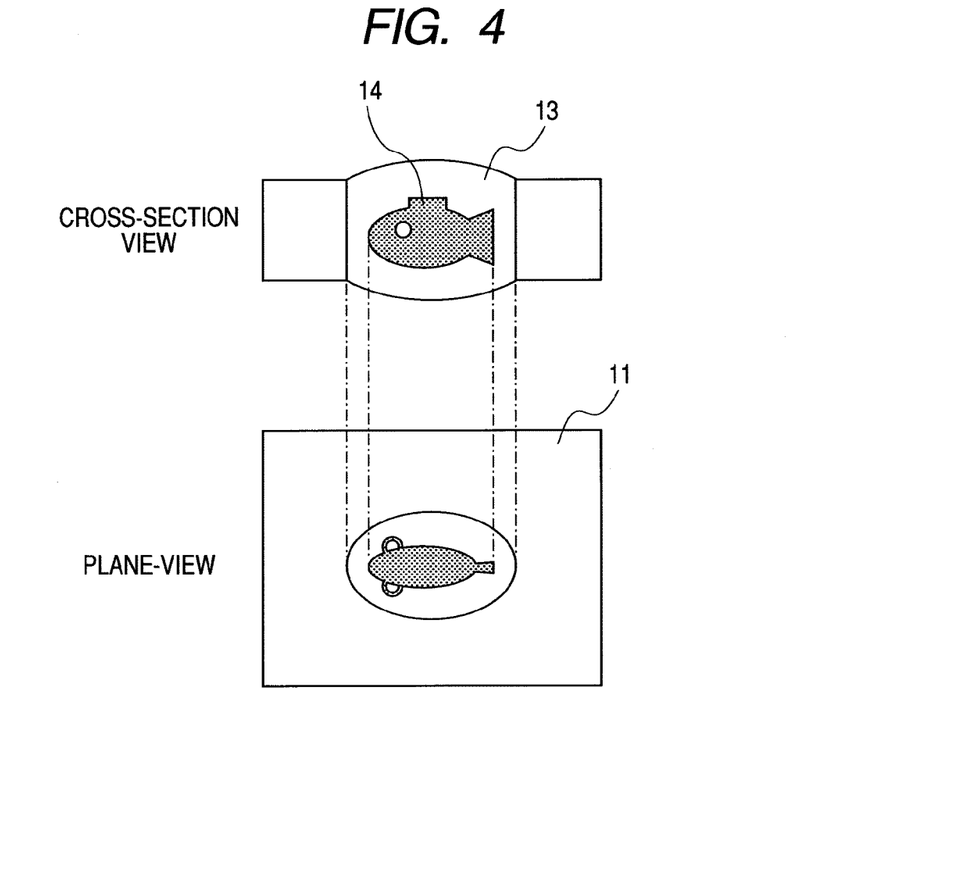
FIG. 4 is a cross-sectional view and a plan view which schematically illustrate the condition in which a biological sample is retained in a penetrating hole through the sample holder of the present invention.

The "sample" handled in this embodiment is not particularly limited as long as the vertical direction thereof is defined by the gravity when the sample is retained in a liquid 13 as shown in FIG. 4. It may include non-biological samples whose vertical direction in a liquid is determined by density distribution within the sample or by gas retained in the sample and biological samples such as cell groups, tissues, organs, oocytes, individual embryos, individuals after hatching or individuals growing from embryos, and plants.

Individuals as the biological samples include vertebrate individuals at every stage through which a fertilized egg become an adult. An embryo refers to an individual at any time stage of hatching at or after fertilization of an egg and prior to becoming an adult. Therefore, eggs (fertilized eggs), larvae and immature individuals are preferable as individual embryos. Examples of the individuals growing from the embryos include individuals in which the embryonic development is advancing from the state of fertilized eggs to hatching and individuals hatched from fertilized eggs such larvae (regarded to have features of adult individuals) in the case of fish and those in the larval stage in the case of amphibians.

Examples of the vertebrates include small animals such as rats and mice as well as large-sized animals such as pigs, dogs, apes or humans, but they are preferably productive animals including amphibians and fishes. From a viewpoint of the maintenance and management of the testing facility, small and productive fishes are preferable. Transparent embryos are preferable since they are easily observed. Moreover, in order to compare effects exerted by a chemical substance on fishes and effects on humans as individuals, it is preferable to use those samples whose genome sequences have been or will be determined in the near future. Particularly preferable examples of such amphibians or fishes include *Xenopus*, tiger puffer, killifish and zebrafish.

Figure 1:
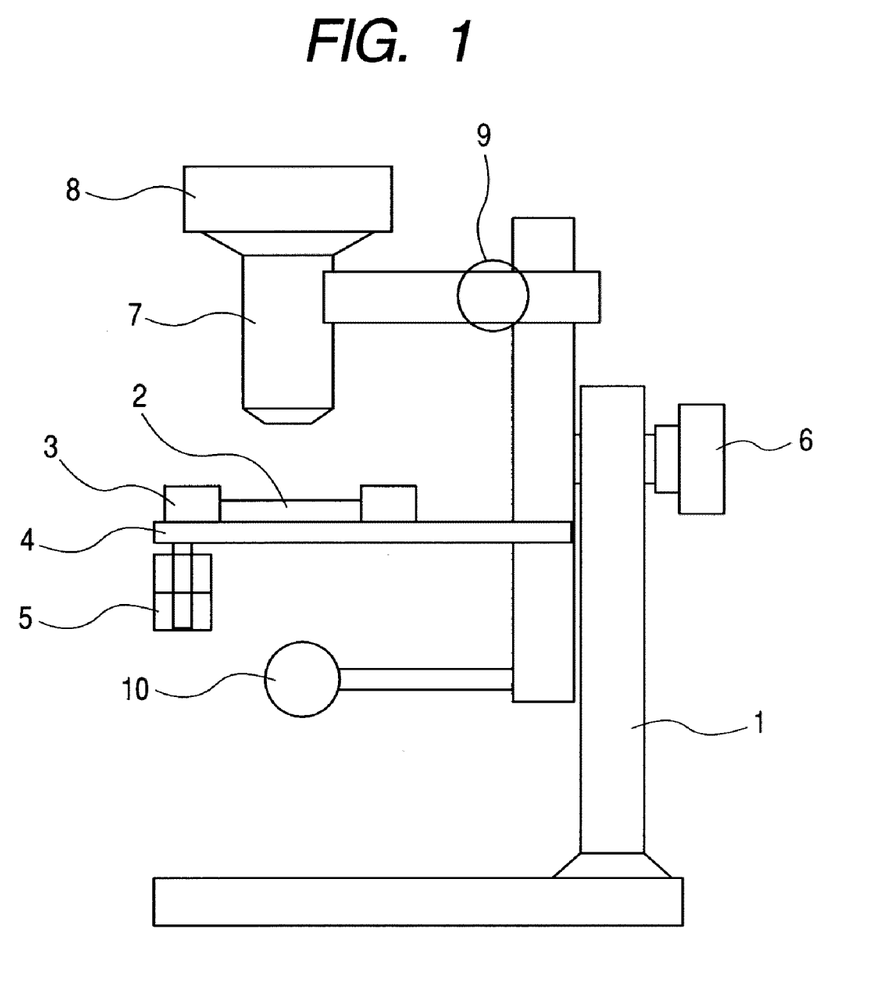
FIG. 1 is a side view illustrating an example of the sample observation system of the present invention.

This embodiment is described below in detail based on FIG. 1. This embodiment includes a support 1, a sample holder 2 rotatably connected to the support 1 through an angle adjusting unit 6, and an observation unit 7. The relative angle between the sample holder 2 and the observation unit 7 is fixed and the observation angle of a sample 14 (see FIG. 4) whose vertical direction is defined by gravity to the direction of the gravity can be adjusted by manipulation of the angle adjusting unit 6.

Figure 2A:
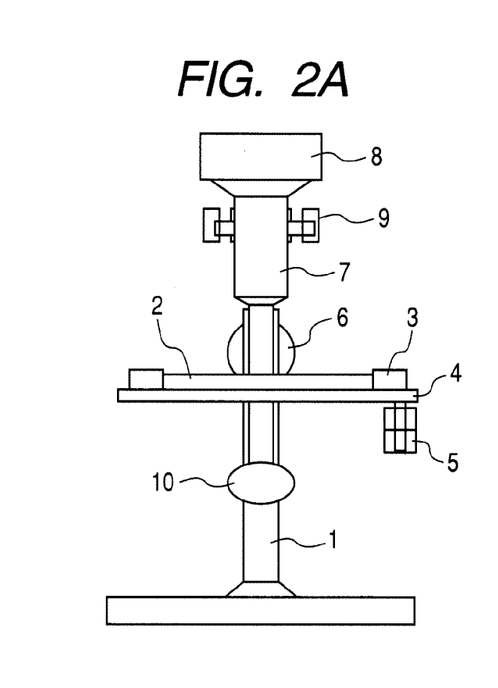
FIGS. 2A, 2B and 2C are an elevational view illustrating the sample observation system of the present invention when the system is used with varied angles of the observation unit of the sample observation system of the present invention.
Figure 2B:
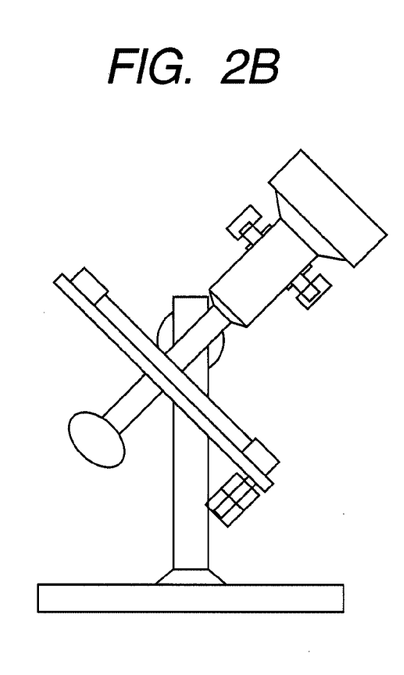
Figure 2C:
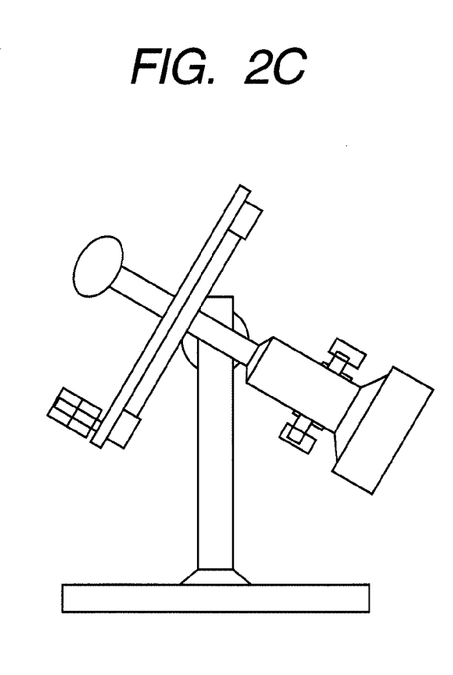

Schematic views according to this embodiment when manipulating the angle adjusting unit 6 are shown in FIGS. 2A to 2C. FIGS. 2A to 2C illustrate observation from directly above (FIG. 2A), observation from above at an angle of about 45 degrees (FIG. 2B), and observation from below at an angle of about 30 degrees (FIG. 2C) to the direction of the gravity which acts on the sample 14. Thus, according to this embodiment, the sample 14 can be freely observed from around the sample 14 at any degree from 0 to 360 degree.

The "condition in which the sample holder and the observation unit have a fixed relative angle therebetween" means a condition in which the angle between the observation unit 7 and the sample holder 2 is fixed and both move integrally by manipulating the angle adjusting unit 6 when observation is performed at different angles to the direction of the gravity which acts on the sample 14. Here, the "relative angle" means a predetermined angle which the sample holder 2 makes to the observation unit 7 when the sample 14 is set. This angle can be adjusted arbitrarily.

By this embodiment, for example, when an oblique observation is appropriate in the aspect of design of the sample holder 2, the sample holder 2 can be attached aslant to the observation direction of the observation unit 7, and then the sample 14 can be observed at any angles to the direction of the gravity which acts on the sample 14 using the angle adjusting unit 6 of this sample observation system. A load against rotation (not illustrated) may be further provided for preventing the sample holder 2 or the observation unit 7 from rotating by their own weights when the angle adjusting unit 6 is rotated.

Figure 3A:
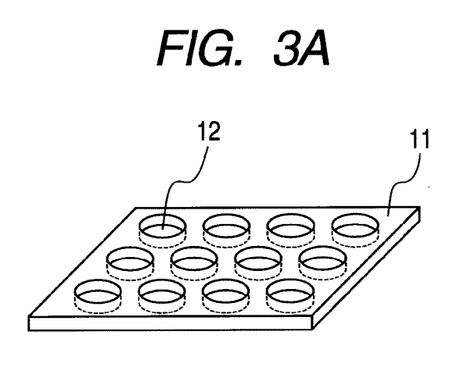
FIGS. 3A and 3B illustrate an example of the sample holder of the present invention.
Figure 3B:
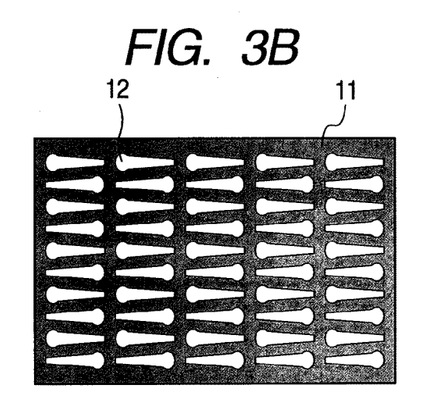

The sample holder 2 used in this embodiment is preferably made detachable from the observation system of this embodiment since such a structure makes easier the manipulation for having the sample 14 retained in the hole 12 (see FIGS. 3A and 3B). Besides, a plurality of the sample holders 2 can be preliminarily prepared to be exchanged one for another, which enables efficient observation of a number of samples 14. The sample holder 2 can be enclosed in a chamber (not illustrated) so that it can be maintained under a constant environment. The above-mentioned chamber can control the internal temperature, humidity, etc. by an apparatus for controlling temperature, humidity, etc.

The sample holder 2 can be attached to a movable holder 4. The movable holder 4 may have XY regulation knobs 5 and the sample holder 2 can be moved therewith in both directions along X-Y axes. The sample holder 2 disposed in the movable holder 4 can be fixed with a sample holder stopper 3 so that it may not be slipped when the observation angle to the sample 14 is varied by the angle adjusting unit 6. In order to minimize any obstruction against the observation of the sample 14, the movable holder 4 of the present invention is preferably transparent or provided with an opening penetrating along the observation direction from the observation unit 7.

The observation unit 7 of this embodiment is a unit for grasping the state and changes of the sample 14 as (an) image(s), and at least includes an objective lens and an image acquisition unit 8. Specifically, the shape of the sample 14 can be observed with the image acquisition unit 8 by irradiating a visible light to the sample 14 retained at the sample holder 2. The image acquisition unit 8 includes ocular lens for directly observing the image or a camera, CCD, etc. for obtaining the image.

It is preferable that a camera is connected and observation is performed by displaying the image of the camera on a monitor from a viewpoint of readiness of observation at the time of adjusting the angle. The observation unit 7 can easily focus on the sample 14 by varying the distance between observation unit 7 and the sample holder 2. For the purpose of varying the distance, either the observation unit 7 or the sample holder 2 may be moved. The focus adjustments knobs 9 for adjusting the focus may be preferably provided, thereby enabling subtle adjustments.

In this embodiment, it is preferable to provide a light source 10. The light source 10 is preferably connected to the observation unit 7 and united with the observation unit 7 so that the angle relation among the light source, the lens and the image acquisition unit may not vary, even if the observation angle is varied by the angle adjusting unit 6. Either an epi-illuminating light source or a transmitting light source may be used as the light source 10.

The present invention may also include a fluorescence observation unit which observes fluorescence from the sample 14. The fluorescence observation unit (not illustrated) irradiates an excitation light to the sample 14 retained at the sample holder 2 from the excitation light source and observes the light-emitting sample 14 with a fluorescence imaging unit. A camera or CCD as well as a scanner etc. can be used for the fluorescence imaging unit. If imaging of the sample 14 is performed in the state where light was made to emit in the interior of the sample 14 by irradiating the sample 14 with an excitation light in this way, the emitting region can be easily detected. Moreover, a living body can also be observed in more detail by uniting a bright field image obtained by irradiating a visible light and a fluorescence image obtained by irradiating an excitation light with an image processing unit.

The second embodiment of the sample observation system of the present invention is an embodiment in which an intervention unit on the sample 14 is added to the first embodiment. The intervention to the sample 14 is performing a labeling or invasive treatment totally or locally on the sample 14. It includes interventions such as chemical interventions by adding a compound such as a drug to the sample 14, optical interventions such as laser irradiation, mechanical interventions such as needle sticking, excision of a part of the sample 14 and ligation, interventions by temperature change, and interventions by electric field. Since this observation system can simply vary the direction of the observation to the sample 14, the intervention unit can be used in combination and the effect of the intervention can be observed from observable any directions over time while performing intervention on a part of the sample 14.

Since the sample 14 is retained in a liquid in this embodiment, chemical interventions and optical interventions which do not need retention (fixation) of the sample 14 at the time of interventions are preferable. Particularly, an optical intervention employing laser can irradiate laser with sufficient accuracy in a portion of the sample 14, it is preferably used for performing a local intervention on the sample 14. As laser interventions, a part of the sample 14 may be lost by ablation, or laser irradiation may be performed on a part of a fluorescence labeled sample 14 to fade locally the fluorescence at the irradiated position. Alternatively, fluorescence labeling may be locally achieved by carrying out laser irradiation to the sample 14 labeled with a chemical substance which emits fluorescence or changes fluorescence wavelength by light irradiation, or to the sample 14 having a protein expressed which emits fluorescence by light irradiation. The lasers irradiation can be also used as an intervention technique by temperature change which gives heat to the whole or a part of the sample 14.

When a local intervention is performed by a chemical intervention, an ink-jet process is preferably employed. When the intervention unit of this embodiment is an intervention unit based on an ink-jet system, an ink-jet process is preferable since it provides for imparting a chemical substance to the sample in a non-contact way and combination of a plurality of kinds of chemical substances or the imparted amount can be freely controlled. Preferably, the chemical substance to be imparted is in a liquid with high viscosity or a chemical substance carried on a sustained-release material which stays at a local site is used so that the chemical substance may not be uniformly distributed into the whole liquid which retains a sample 14 from an imparted site.

Since this observation system can simply vary the direction of the observation to the sample 14, the intervention unit can be used in combination and the effect of the intervention can be observed from any directions over time while performing intervention on a part of the sample 14. Therefore, although such intervention unit (not illustrated) can be independently provided in this observation system, it is preferably provided so that the relative angle to the observation unit 7 is fixed. On this account, interventions can be performed from any observable directions to the direction of the gravity which acts on the sample 14 as in the observation unit 7. In addition, as long as the relative angle with the observation unit 7 is fixed, the intervention unit may perform an intervention and observation to the sample 14, simultaneously or at a time lag therebetween.

Specifically, the intervention unit and the observation unit 7 can be provided in parallel at an interval distance between the holes 12 and after performing an intervention to the sample 14 by the intervention unit, the results of the intervention can be observed by the observation unit 7. In addition, the results of such an intervention on the same sample 14 can be observed on real time by adjusting the relative angle so that the intervention and observation may be simultaneously performed on the sample 14 of the same hole 12.

Hereinbelow, the sample holder 2 used in the sample observation system of the present invention is described in detail. An example of the sample holder of the present invention is illustrated in FIGS. 3A and 3B. The sample holder 2 has a hole (opening) 12 which penetrates the base (substrate) 11.

Any material can be used for the material of the base 11 of the sample holder 2 as long as it is a material which can form a hole 12. For example, metals such as iron, copper and aluminum, or alloys including these, and ceramics such as glasses, alumina and silicones, plastic resins such as Teflon (registered trademark), polyethylene, polypropylene, polyester, polyacetal, silicone rubber, polycarbonate, polyvinyl chloride, polystyrene and nylon, or composite materials thereof can be used. However, the material of the base 11 is preferably a material which basically does not dissolve in water or the components thereof does not elute in water. The inner wall of the hole 12 of the sample holder 2 may be subjected to a hydrophilization treatment or a roughening treatment so that it may be apt to retain a liquid. Although the color of the material of the surface of the sample holder 2 is not particularly concerned about, a material which suppresses reflection of light at the time of observation by the observation unit 7, and a material which does not have fluorescence in itself when performing fluorescence microscopy etc. also are preferable.

Although the number of the hole(s) 12 of the sample holder 2 is not particularly limited, a plurality of holes can be provided in the base 11. Providing a plurality of holes 12 increases the number of the observable samples 14 simultaneously. When the observation unit is an image forming unit, it is preferable that the base 11 has a plane so that all the samples may be well focused in the focal plane of the image forming unit. The plane part can be easily provided by using the base 11 in the shape of a sheet or a plate. The hole 12 is designed so that a sample 14 can be retained along with a liquid 13. A liquid 13 is retained by the interaction power (adhesion) of a liquid to the inner walls of the hole 12 of the sample holder 2. Furthermore, it is surmised that the sample 14 is retained with surface tensions of the liquid in the state where the sample is wrapped with the liquid 13.

An example is shown in FIG. 4, in which the sample 14 is in the shape of a fish and the hole 12 is oval. The cross-sectional view and plan view schematically illustrate the state in which the sample 14 is retained along with a liquid 13 within the hole 12. The hole 12 preferably has the size which can retain only one sample 14 and cannot retain two samples, since in that case, no overlapping of the samples 14 takes place but good image can be obtained.

In the present invention, it is preferable that the hole 12 has a suitable open area depending on the sizes of the sample 14 and has an appropriate thickness. That is, in order to retain one sample 14 stably efficiently in a hole 12, the size (dimension) of the hole, i.e., opening area and thickness, influences greatly. The shape of the hole 12 may be any shape selected from polygons such as quadrangles, ellipse shapes and star-like shapes in addition to the circular shape illustrated in FIG. 1 as long as the hole 12 has an open area sufficient for retaining one such object stably efficiently along with a liquid.

The open area of each hole 12 is preferably in the range of 1.05 to 2.63 times of the maximum cross-sectional area of the target sample 14. It is more preferable that the open area of each hole 12 is in the range of 1.2 to 2.25 times of the maximum cross-sectional area of the sample 14 in order to stably retain the sample 14 while increasing the probability of retaining one sample in every hole 12. The maximum cross-sectional area of the sample 14 means the cross-sectional area containing the center of gravity of the sphere if it is a sphere or semisphere such as an egg. When the sample 14 is a fry or an amphibian larva, the cross-sectional area thereof means the lateral (horizontal) cross-sectional area of such a fry, etc. in the posture which it can take stably in the hole 12 in which it is retained along with a liquid 13.

The size in which two or more objects cannot be retained refers to at least the size in which the maximum section of the two objects cannot be disposed in the hole 12 geometrically. If the open area of the hole 12 is less than 1.05 times of the maximum cross-sectional area of the sample 14, the sample 14 will be hard to be disposed along with a liquid 13 in the hole 12 and it exceeds 2.63 times, there may be increasing cases where a plurality of samples 14 are disposed in a liquid 13. Holes 12 with a plurality of different opening areas may be provided in the same base 11.

The thickness of the base 11 does not have to be necessarily uniform. However, the thickness in the vicinity of the hole 12 is preferably 0.2 to 1.9 times of the maximum thickness of the target sample 14 respectively for the purpose of disposing only one sample 14. The maximum thickness of the sample 14 means the radius of the maximum cross-sectional area for the sphere or semisphere such as an egg. When the sample 14 is a fry or an amphibian larva, the maximum thickness thereof means the vertical thickness of such a fry, etc. in the posture which it can take stably in the hole 12 in which it is retained along with a liquid 13.

For example, when an egg cell having a diameter of about 1 mm is retained, the thickness of the hole 12 is preferably in the range of 0.2 to 1.9 mm. When it is less than 0.2 times of the maximum thickness (diameter in the case of a sphere) of the sample 14, the sample cannot be retained stably since the volume of the liquid 13 is too small for retaining the sample 14 and the ratio of the samples which drop out when disposing the samples will increase. In the meantime, when it exceeds 1.9 times of the maximum thickness (diameter in the case of a sphere) of the sample 14, the ratio of retaining a plurality of samples will increase.

The sample holder 2 has a plurality of holes 12 which penetrate the base 11. Although they may be disposed in any area of the base 11, it is preferable to dispose them regularly for automation of the testing and treating of the samples 14 described later. There is no limit at all about the number and disposition density of the holes 12 provided in one base 11. From the aspect of manipulation, it is preferable that disposition density is in the range of 10 to 100 holes/cm$^2$ if the diameter of the hole 12 is approximately 1 mm. That is, if it is less than 10 holes/cm$^2$, surface areas without holes are too large and liquid droplets will be easily isolated in these areas. Therefore, objects may be disposed in the areas other than the holes 12 along with these liquid droplets, and the disposition efficiency decreases. On the contrary, if it exceeds 100 holes/cm$^2$, the distance between the holes 12 is insufficient and contamination, for example, mixing of a liquid which retains the object with a retaining liquid in the adjacent hole 12 in the subsequent handling is likely to occur. That is, the ratio (aperture ratio) of the opening areas of the holes 12 to the areas of the sample holders 2 of the present invention is preferably fall under the range of 7.9%-78.5%.

Although it is preferable to retain one target sample 14 in each of a plurality of the holes 12 of the sample holder 2, respectively, it is not necessarily to retain a sample 14 in all the holes 12 of the sample holder 2 in the present invention. However, if the ratio of holes 12 which retain the sample 14 decreases extremely, efficiency for observing the sample 14 later decreases.

The sample holders employed in the observation systems of the present invention are characterized by having penetrating holes 12. This is advantageous as compared with conventional wells having a bottom in i) that disposing samples is simple; ii) that taking out the samples is simple; iii) since the samples does not touch the bottom plate, they are not affected by the stimulus, etc. from the bottom plate during the growth; iv) since the surface area through which the liquid in the holes contacts with the outside air is large, gas exchange is simple to be performed; and v) that since there is no bottom plate, there are no noise factors due to the bottom plate such as reflecting light and self-fluorescence in the observation step.

The process of retaining the sample 14 of this embodiment may be one using a sample holder 2 of the present invention, in which samples 14 such as embryos can be simply disposed. Specifically, samples 14 can be easily disposed into the holes 12 one for one along with a liquid 13 by contacting the liquid 13 having the samples 14 dispersed therein with the sample holder 2. The size of the hole 12 is one which can retain one target sample 14 but cannot retain two or more samples 14.

Examples of the process of contacting the liquid 13 which contains the samples 14 with the sample holders 2 include a process of pouring the liquid 13 which contains the samples 14 onto the sample holder 2 from above, and a process of immersing the sample holder 2 in the liquid 13 which contains the samples 14. As one of a process of pouring the liquid 13 which contains the samples from above, a conventional slit type application apparatus can be employed, by which the liquid 13 can be uniformly placed all over the sample holder 2 from the slit die. In addition, the excessive liquid 13 after contact can be simply removed by tilting the sample holder 2, or wiping off the rear with a blade, or spraying air. However, in the case of spraying air, it is necessary to control the air pressure and spraying angle so as not to blow away the samples 14 retained in the holes 12. If the excessive liquid 13 is present so that it may connect the liquid in a plurality of holes 12, contamination tends to occur between the holes 12. Besides, the samples 14 may easily be retained on the area other than the holes 12. Therefore, it is preferable to leave no or as least droplets as possible of the liquid 13 on the area other than the holes 12.

It is preferable that at least one of the surfaces of the sample holder 2 is hydrophobic. If at least one of the surfaces of the sample holder 2 is a hydrophobic surface, an aqueous liquid is flipped on the area other than the holes 12 and the excessive liquid 13 can be removed easily. In that case, the contact angle of the liquid 13 on the hydrophobic surface may be generally 90 degrees or more.

In order to retain the samples in the sample holder 2 with surface tension of the liquid 13, the liquid having surface tension of 25 mN/m or more is generally preferable. When it is not more than 25 mN/m, the samples 14 will become hard to be retained in the holes 12 along with the liquid 13, and will also fall out more often by a slight vibration. The liquid 13 to be retained in the sample holder 2 along with the samples 14 is preferably an aqueous liquid having high affinity to the samples 14 and readily adhering to the inner walls of the holes 12.

The above-mentioned aqueous liquid includes aqueous liquids such as water or alcohols, glycol solvents, or glycerin and aqueous solutions containing these aqueous liquids, and in the case of the aqueous solution, it is preferable that 50% or more of water is contained. Furthermore, for the purpose of preventing evaporation of the liquid 13 retaining the sample 14 from the sample holder 2 or stabilizing the retention of the sample, at least one of moisturizers, surface tension adjustment agents or thickeners can be added.

As examples of the above-mentioned moisturizers, one or more of polyhydric alcohols such as glycerin, propylene glycol, butylene glycol and sorbitol, mucopolysaccharides such as hyaluronic acid and chondroitin sulfate, and protein hydrolysates of soluble collagen, elastin and keratin, etc. can be singly used or mixed and used.

As examples of the above-mentioned surface tension adjustment agents, one or more of anionic, cationic, amphoteric or nonionic surface-active agents can be added. However, it is preferable that the surface tensions of the liquid is 25 mN/m or more.

The examples of the thickener include starches such as oxidation modified starch, enzyme modified starch, thermochemically modified starch, cationized starch, amphoteric starch, etherified starch, cellulose derivatives such as carboxymethyl cellulose, hydroxyethylcellulose and ethylcellulose, natural or half-synthetic polymers such as casein, gelatin and soy protein, water-soluble polymer compounds such as polyvinyl alcohols including completely or partial saponified polyvinyl alcohol, acetoacetylated polyvinyl alcohol, carboxy modified polyvinyl alcohol, olefin modified polyvinyl alcohol and silyl modified polyvinyl alcohol, and at least one of these water-soluble polymer compounds can be appropriately selected and used.

In the present invention, the viscosity of the liquid 13 used is preferably not less than 0.1 Pa·s (pascal second), and this may be achieved by adding a thickener mentioned above if needed. In addition, if it is also required to control to the salt concentration or pH suitable for a living body, salts such as sodium chloride and various pH adjusters and preservatives and antibacterial agents can also be suitably added.

A sample observation process which is the third embodiment of the present invention is a sample observation process in which vertical direction is defined by the gravity. This process includes retaining a liquid containing a sample in a sample holder having at least one penetrating hole; and observing the sample in a condition in which an observation unit for observing the sample and the direction of the gravity which acts on the sample have an arbitrary angle therebetween in a condition in which the sample holder and the observation unit have a fixed relative angle therebetween.

The sample holder and the penetrating hole provided on the sample holder and so on referred to in this embodiment may be the same sample holder and so on which are used in the first embodiment of the present invention. The definitions of "have a fixed relative angle therebetween" and the "relative angle" also refer to the same state and angle as in the first embodiment. Observation of the sample in a condition in which the observation unit and the direction of the gravity which acts on the sample have an arbitrary angle therebetween and further in a condition in which the sample holder and the observation unit have a fixed relative angle therebetween means that the sample 14 can be freely observed from around the sample 14 whose vertical direction is defined by gravity at any degree from 0 to 360 degree.

As described above, the present invention is also useful as a process for observing a plurality of samples simultaneously.

That is, the process includes disposing a plurality of biological samples respectively in positions on a plane which positions correspond to focal fields of an image acquisition unit; and rotating both the image acquisition unit and the plane around an axis on the plane while keeping the positional relationship of the image acquisition unit and the plane.

The apparatus for observing a plurality of samples simultaneously has an image acquisition unit; a holder for disposing a plurality of biological samples respectively in positions on a plane which positions correspond to focal fields of the image acquisition unit; and a rotation mechanism for rotating both the image acquisition unit and the plane around an axis on the plane while keeping the positional relationship of the image acquisition unit and the plane.

The above construction enables to observe a plurality of biological samples from various directions simultaneous.

EXAMPLE

Hereinbelow, the present invention is specifically described by way of a working example but the present invention is not limited to this.

Example 1

Next, an observation system and an observation process in the case of using a larva of a zebrafish as a (biological) sample 14 is described by way of a working example.

Preparation of Sample Holder

A Teflon (registered trademark) sheet having a size of 100 mm×150 mm with a thickness of 0.7 mm was cut out to obtain a sheet containing holes in the shape made similar to a profile of a larva as illustrated in FIG. 3B. Sixty (60) holes 12 (matrix having 12 rows and 5 columns) were formed so that the holes 12 might be disposed at equal intervals.

Placement of Sample

After contacting 50 ml of an aqueous suspension of zebrafish larvae (20 embryos/ml) on the 7th day after fertilization with the sample holder 2 by pouring the aqueous suspension from above, excessive liquid was removed from the sample holder 2 and thereby zebrafish larvae were retained in each of the holes 12 of the sample holder 2 along with the liquid. The excessive liquid on the sample holder 2 was made to fall out by tilting the sample holder 2 so that no droplets might remain in positions other than the holes (openings) 12.

Observation of Sample

The sample holder 2 in which the samples were disposed was mounted on a movable holder 4 of the observation system, and it was fixed with a sample holder stopper 3. The observation images were displayed on the monitor using a CCD camera (NIKON DS-2Mv) provided in the observation unit 7, while irradiating the sample holder 2 with a visible light. The sample observed was selected with XY regulation knob, and the focus was adjusted. Next, the bright field images were taken varying the angle from the horizontal direction to the gravitational direction to the vertical to direction by manipulating the angle adjusting unit 6.

Figure 5:
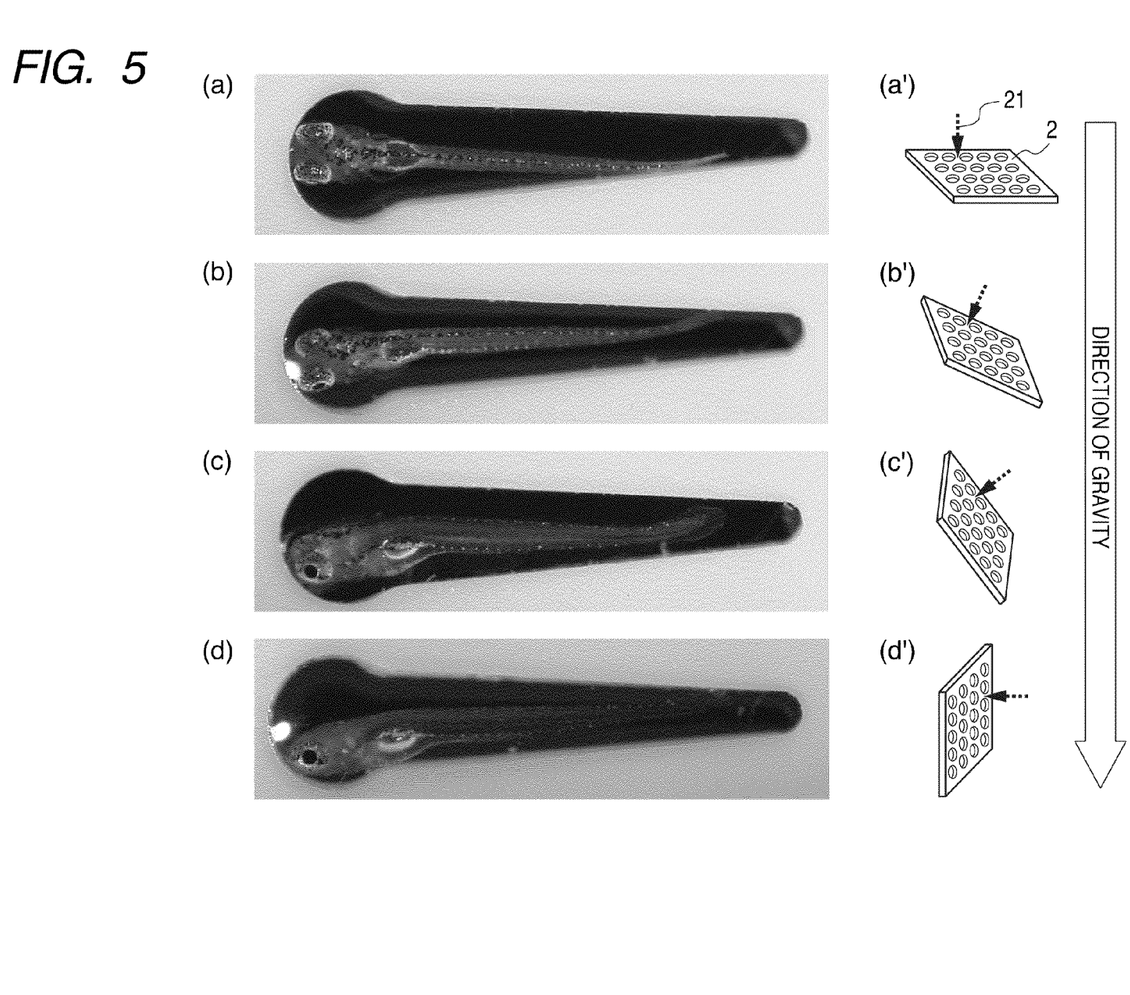
FIG. 5 shows biological sample images observed in Example 1 of the present invention and observation directions therein.

The bright field images were shown by photos (a) to (d) in FIG. 5 in which a larva retains a posture vertical to the horizontal direction by gravity (from (a') to (d') in FIG. 5). By employing the observation system of the present invention, observation of a zebrafish larva which retains a posture by gravity was carried out while adjusting the observation direction simply from 0 degrees to 360 degrees.

The present invention provides an observation process and an observation system which enable observation of a biological sample having a direction, for example, internal organs, tissues or cancers in a predetermined state without giving stress to the biological sample from an appropriate direction in the elucidation of a living body function, diagnosis of diseases or evaluation of medical drugs to diseases. They can serve as an apparatus for rapid drug screening and safety assessments of chemical substances.

The present invention is not limited to the above embodiments and various changes and modifications can be made within the spirit and scope of the present invention. Therefore to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-131628, filed May 29, 2009, which is hereby incorporated by reference herein in its entirety.

What is claimed is:

1. A sample observation system of a sample whose vertical direction is defined by gravity, the system at least comprising:
    a sample holder having at least one penetrating hole for retaining a liquid containing the sample;
    an observation unit for observing the sample; and
    an angle adjusting unit for varying the angle of the observation unit to the direction of the gravity which acts on the sample in a condition in which the sample holder and the observation unit have a fixed relative angle therebetween.

2. The sample observation system according to claim 1, wherein the hole has a size which can retain only one sample and cannot retain two or more samples.

3. The sample observation system according to claim 1, further comprising a mean to intervene for the sample.

4. The sample observation system according to claim 1, wherein the sample holder is in the shape of a plate having a plane on which openings of the holes are disposed, and the observation unit is an image acquisition unit which can focus on the plane.

5. A sample observation process of a sample whose vertical direction is defined by gravity, the process comprising:
    retaining a liquid containing the sample in a sample holder having at least one penetrating hole; and
    observing the sample in a condition in which an observation unit for observing the sample and the direction of the gravity which acts on the sample have an arbitrary angle therebetween further in a condition in which the sample holder and the observation unit have a fixed relative angle therebetween.

6. A process for observing a plurality of samples simultaneously, comprising:
    disposing a plurality of biological samples respectively in positions on a plane which positions correspond to focal fields of an image acquisition unit; and
    rotating both the image acquisition unit and the plane around an axis on the plane while keeping the positional relationship of the image acquisition unit and the plane.

7. An apparatus for observing a plurality of samples simultaneously, comprising:
    an image acquisition unit;
    a holder for disposing a plurality of biological samples respectively in positions on a plane which positions correspond to focal fields of the image acquisition unit; and
    a rotation mechanism for rotating both the image acquisition unit and the plane around an axis on the plane while keeping the positional relationship of the image acquisition unit and the plane.

* * * * *